United States Patent [19]

Bauman

[11] Patent Number: 4,579,108

[45] Date of Patent: Apr. 1, 1986

[54] LARYNGOSCOPE BLADE AND DISPOSABLE COVER

[76] Inventor: Jack Bauman, 1677 San Onofre Dr., Pacific Palisades, Calif. 90272

[21] Appl. No.: 687,506

[22] Filed: Jan. 4, 1985

Related U.S. Application Data

[63] Continuation of Ser. No. 472,975, Mar. 7, 1983, abandoned.

[51] Int. Cl.[4] ................................................ A61B 1/26
[52] U.S. Cl. .................................................... 128/10
[58] Field of Search ........................ 128/10, 11, 200.26

[56] References Cited

U.S. PATENT DOCUMENTS 3,426,749  2/1969  Jephcott ................................ 128/11
3,826,248  7/1974  Gobels .................................. 128/11

*Primary Examiner*—Edward M. Coven
*Assistant Examiner*—Max F. Hindenburg

*Attorney, Agent, or Firm*—Fulwider, Patton, Rieber, Lee & Utecht

[57] ABSTRACT

An improved laryngoscope blade is shaped similarly to a conventional blade except that a downwardly extending fin and lateral portion is not used. Rather an integral sleeve of plastic material is provided and receivable over the front portion of the blade in the manner of a stocking. This plastic sleeve has a solid downwardly extending fin portion and a lateral extending portion. The plastic cover or sleeve serves two functions: first, it removes the necessity of sterilizing the laryngoscope blade itself since the sleeve can be removed and disposed of after each use; second, the extended fin and lateral portion of the sleeve serves as a second surface to cushion contact of the blade with a patient's upper front teeth should these teeth be used unconsciously as a fulcrum when manipulating the blade to expose the larynx in order to facilitate insertion of an endotracheal tube.

6 Claims, 8 Drawing Figures

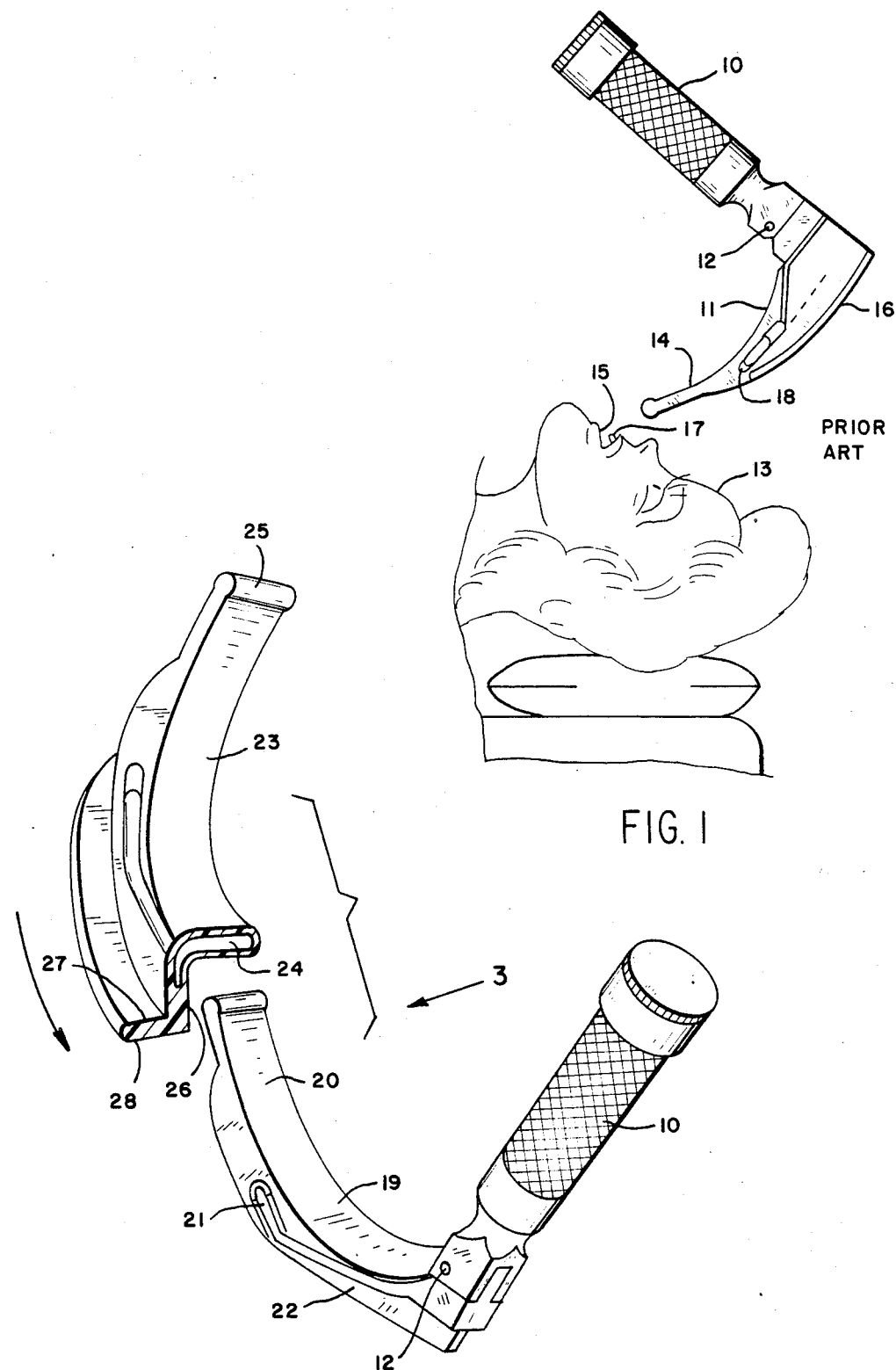

LARYNGOSCOPE BLADE AND DISPOSABLE COVER

This application is a continuation of application Ser. No. 472,975, filed Mar. 7, 1983, now abandoned.

FIELD OF THE INVENTION

This invention relates generally to medical instruments and more particularly to an improved laryngoscope blade and disposable cover primarily used to facilitate insertion of an endotracheal tube in a patient.

BACKGROUND OF THE INVENTION

Most laryngoscopes generally comprise a laryngoscope blade and cooperating handle, both made of metal. These two items are connected together to form a general L-shape. The handle normally serves as an enclosure for batteries for energizing an appropriate light bulb secured adjacent to the blade in manner to illuminate the patient's mouth and larynx entrance areas. A first surface on the blade itself is used to lift the tongue and mandible of a patient when the patient is in a supine position or depress the the tongue and mandible of the patient if the patient is in an upright position. This action prevents the patient's tongue from obstructing the channel of vision.

While the instrument is useful for examining the larynx, its primary function is to expose the larynx in a manner to facilitate the insertion of an endotrachael tube. In this respect, the patient usually is in a supine position on an operating table with his or her head extended backward. In this position, as described, the first surface of the laryngoscope blade is used to effectively lift the tongue and mandible upwardly to expose the larynx, the light on the blade being positioned beneath the lifting first surface of the blade. A second surface of the blade spaced rearwardly of the first surface is in a position opposing the upper front teeth of the patient.

In using the laryngoscope, there is almost invariably an unconscious tendency to use the upper front teeth of the patient as a fulcrum for the blade in exposing the larynx. Because of the metal construction of the blade, the patient's front teeth often are chipped by such contact and occasionally the teeth may be broken or knocked out.

In addition to the foregoing problems conventional laryngoscopes should be sterilized after each use, or at a minimum the blade for the laryngoscope must be detached from the handle and sterilized.

In my copending patent application, Ser. No. 331,164 filed Dec. 16, 1981, and entitled LARYNGOSCOPE BLADE now abandoned, I describe an improved laryngoscope blade wherein that portion of the conventional laryngoscope blade defining the referred to second surface opposing the upper front teeth of the patient is removed and a plastic material substituted for the removed portion.

This plastic material is capable of flexing in a manner to cushion contact with the patient's upper front teeth should the same be used unconsciously as a fulcrum when manipulating the blade to expose the larynx. The plastic material is secued to the remaining portion of the blade in a manner to function as an integral part of the blade.

While the problem of damaging teeth is solved to a large extent by my above-described improved laryngoscope blade, there still remain problems of sterilization and also added expense in the actual manufacture of the blade wherein compound materials are used.

In my design Pat. No. 242,396 I disclose a unique shaping and contouring for a disposable cover to be used to cover a laryngoscope blade. This issued design patent together with my above-mentioned copending patent application constitutes the closest prior art to the present invention of which I am aware.

BRIEF DESCRIPTION OF THE PRESENT INVENTION

With the foregoing in mind, the present invention contemplates the provision of a laryngoscope blade and disposable cover wherein both problems of sterilization and risk of damaging a patient's teeth essentially are avoided.

More particularly, in accord with the present invention, in its broadest aspect, a laryngoscope blade has a first surface portion defining a first surface for lifting the tongue and mandible of a patient when upside down, and a second portion defining a fin spaced rearwardly of the first surface, and extending towards the upper front teeth of the patient. A cover comprises an integral sleeve of plastic material having a rear opening for receiving the first portion of the laryngoscope blade. This sleeve is shaped in a corresponding manner to the first portion of the blade so that it can be slid over the blade in the manner of a stocking by urging it rearwardly over the front end of the blade. The portion of the plastic sleeve overlying the second portion of the blade includes a solid portion extending beyond the blade fin and thence laterally of the fin to define a second surface opposing the upper front teeth of the patient. With this arrangement, this second surface will cushion contact with the teeth should the same be unconsciously used as a fulcrum when manipulating the blade to expose the patient's larynx. The patient's teeth are thus protected. Further, the plastic sleeve can easily be slid off from the blade after use and disposed of so that the laryngoscope itself need not be sterilized and is available to receive another cover which is of the same construction as the first mentioned cover and is sterile.

BRIEF DESCRIPTION OF THE DRAWINGS

A better understanding of this invention will be had by now referring to the accompanying drawings in which:

FIG. 1 is a fragmentary view of a patient with her head tilted back preparatory to having her larynx exposed for insertion of an endotracheal tube by means of conventional laryngoscope blade typical of the prior art;

FIG. 2 is an enlarged, exploded perspective view of a modified laryngoscope blade and disposable cover in accord with the present invention;

DETAILED DESCRIPTION OF THE PREFERRED EMBODIMENT

Figures 3, 4:
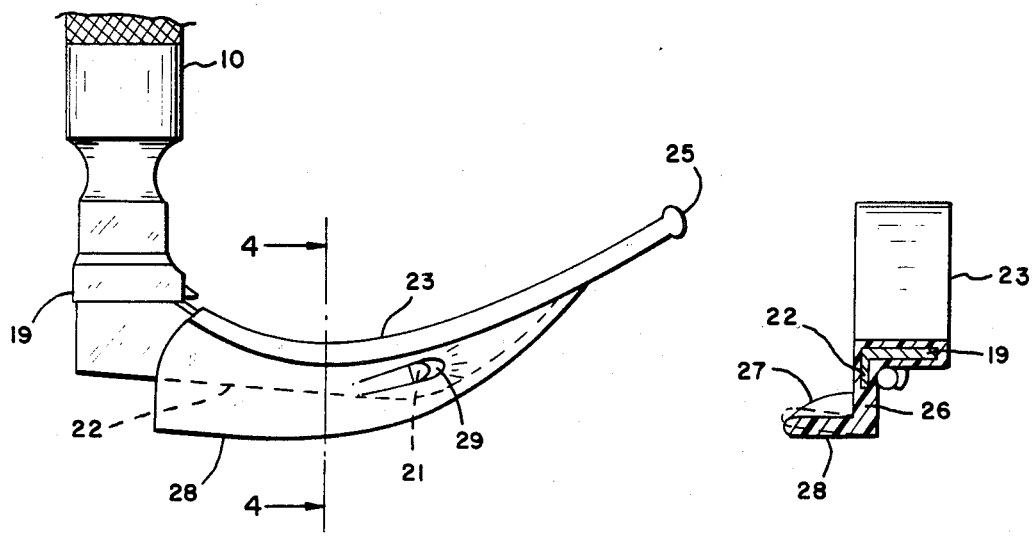
FIG. 3 is a side elevation of the laryngoscope with the disposable cover in place looking in the direction of the arrow 3 of FIG. 2.
FIG. 4 is a cross section taken in the direction of the arrows 4—4 of FIG. 3.

Referring first to FIG. 1, there is shown a conventional laryngoscope including a handle 10 and blade 11 coupled as by pivot rod 12 to one end of the handle to define therewith a general L-shape.

Also shown in FIG. 1 is a patient 13 with her head in a supine position preparatory to the insertion of an endotracheal tube. In this procedure, a first surface 14 of the blade 11 is used to depress the patient's tongue and mandible 15. A second surface 16 spaced rearwardly of the first surface, in turn, is in a position opposing the patient's upper front teeth shown at 17.

In the particular example in FIG. 1, the blade 11 constitutes a MacIntosh blade and includes a lightbulb 18 beneath the first surface 14 in a position to illuminate the channel of vision when the laryngoscope is used.

As already described briefly heretofore, in using the laryngoscope there is an unconscious tendency to encroach upon the patient's upper front teeth 17 with the second surface 16 of the blade. In other words, the teeth 17 of the patient are used as a fulcrum for the blade in exposing the larynx in order to insert an endotracheal tube. Since the conventional laryngoscope blade shown is of metal and is hard, the teeth of the patient can be chipped or otherwise seriously damaged.

Referring now to FIG. 2, there is illustrated the improved laryngoscope blade together with a disposable cover in accord with the present invention. More particularly, the improved blade is indicated at 19 and, as in the case of the blade 11 described in FIG. 1 is elongated and of high strength rigid material. The same handle 10 and pivot pin 12 described in FIG. 1 may be used to couple the modified blade 19 to one end of the handle as shown so that a similar general L-shape results.

Blade 19 has a first portion defining a first surface 20 again used for lifting the tongue and mandible of a patient when supine and light bulb 21 beneath this surface. Blade 19 further includes a second portion defining an integral wall which might be straight or sometimes curved constituting a fin 22 extending in a direction opposite to the first surface 20 and spaced rearwardly thereof so as to extend towards the upper front teeth of the patient. In this respect, the blade 19 is different from the blade 10 of FIG. 1 in that the second surface 16 below the blade light bulb 18 of FIG. 1 does not exist on the blade 19 of FIG. 2.

Still referring to FIG. 2 and in accord with the present invention, there is provided a cover in the form of an integral sleeve 23 of thin plastic material having a rear opening 24 for receiving the first portion or forward end of the laryngoscope blade 19. The sleeve 23 is shaped in a corresponding manner to the first or forward portion of the blade so that it can be slid over the blade in the manner of a stocking by urging it rearwardly in the direction of the arrow until the front end of the blade reaches the closed front end of the sleeve shown at 25.

As will be clearer as the description proceeds, the plastic sleeve 23 material overlying the second portion of the blade 19; that is, the fin portion 22 is reinforced by making the plastic material solid as indicated at thickened web 26. This reinforced portion extends beyond the fin 22 when the sleeve is in place and thence laterally of the fin to form a thickened reinforced plastic flange as shown at 27 to define a second surface 28 which will oppose the upper front teeth of the patient when the sleeve is in position. This surface will cushion contact with the teeth should the same be used unconsciously as a fulcrum when manipulating the blade to expose the patient's larynx.

Referring specifically to FIG. 3, the sleeve 23 is shown in place wherein it will be noted that the second portion of the blade constituting the fin 22 is covered by the sleeve, the sleeve itself extending further downwardly and thence laterally; that is, out of the plane of the drawing as viewed in FIG. 3 so as to define the second surface 28.

The sleeve in FIG. 3 may be transparent or include a portion 29 which is transparent overlying the light exit area for the blade light 21 described in FIG. 2. With this arrangement, light is available when using the laryngoscope with the sleeve in place.

In the cross section of FIG. 4, the action of the sleeve 23 in cushioning the action of the blade against the patient's teeth will be better understood. As shown, the second surface 28 of the lateral extending portion 27 of the sleeve is capable of flexing as indicated by the dotted line position of this lateral portion when under pressure. The flexing is a consequence of there not being provided any rigid blade portion of the blade 19 within the lateral area of the sleeve. In this respect, and as noted heretofore, the blade 19 differs from the conventional laryngoscope blade illustrated in FIG. 1.

Figure 5:
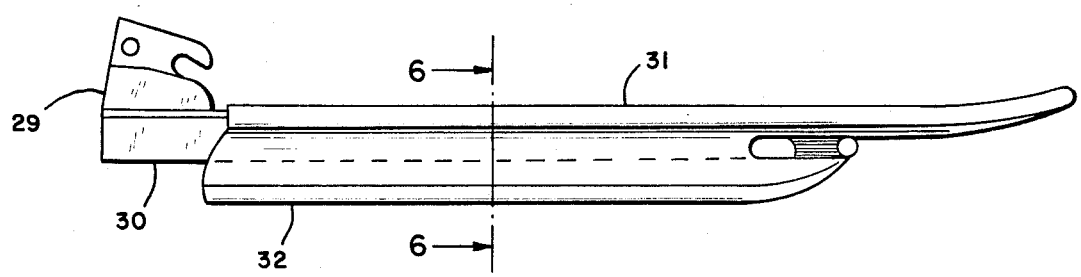
FIG. 5 is a side elevational view of another type of laryngoscope blade with a plastic cover.

The present invention is applicable to blades other than the MacIntosh type. By way of example, there is illustrated in FIG. 5 a blade 29 of the Guedel type which is substantially straight when compared to the MacIntosh blade. This Guedel type blade is modified by removing a lower portion thereof as viewed in FIG. 5 to leave a fin 30. A plastic sleeve 31, in turn, slides over the blade in the same manner as described for the MacIntosh blade and includes a solid reinforced portion extending beyond the fin 30 and thence laterally to define a second surface 32.

Figure 6:
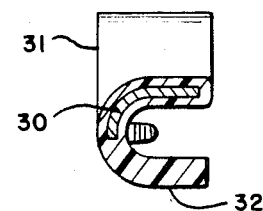
FIG. 6 is a cross section taken in the direction of the arrows 6—6 of FIG. 5.

The foregoing is better illustrated in the cross section of FIG. 6 wherein the plastic sleeve 31 follows in cross section the normal cross section of the Guedel type blade except that the second surface 32 which would normally be opposing the patient's teeth is of plastic material which will cushion engagement with the teeth and thus serve the same purpose as the corresponding portion of the sleeve utilized with the MacIntosh blade described in FIGS. 1 through 4.

Figure 7:
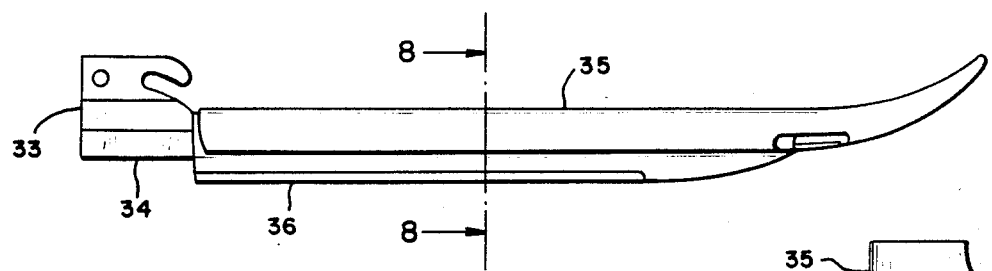
FIG. 7 is a side elevational view of yet another type of laryngoscope blade with a plastic cover; and, FIG. 8 is a cross section taken in the direction of the arrows 8—8 of FIG. 7.

FIG. 7 shows yet another blade 33 of the Miller type wherein again a portion of the lower part of the blade has been cut away to define a fin 34. A plastic sleeve 35 is again slid over this portion of the blade and includes an extending solid portion defining a second surface 36 to replace the metal portion formerly occupying this space.

Figure 8:
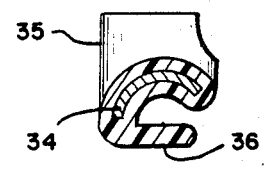

Referring to the cross section of FIG. 8, the contouring is similar to the Miller type blade before the bottom portion thereof has been cut away. This bottom portion as is clear from FIG. 8 is replaced by the solid plastic part of the sleeve 35 defining the second surface 36.

As in the case of the MacIntosh type blade and cooperating plastic sleeve, the plastic sleeves 31 and 35 of FIGS. 5 and 7 provide for the desired cushioning action to protect the patient's teeth as by flexing of the second surface portions 32 and 36 respectively. Also, the sleeves are disposable after use so that sterilization of the blade itself is not necessary.

From all of the foregoing, it will now be evident that the present invention has provided a greatly improved laryngoscope blade and disposable cover wherein both prior art problems of sterilization and risk of damage to a patient's teeth are solved simultaneously.

Various changes falling within the scope and spirit of this invention will occur to those skilled in the art. The laryngoscope blade with disposable cover accordingly is not to be thought of as limited to the specific embodiments for the various type blades set forth for illustrative purposes.

I claim:

1. In a laryngoscope having a rigid blade and a disposable cover therefor wherein the blade has a tongue engaging lower flange and wherein the cover comprises an integral sleeve having a proximal and distal end and formed from a plastic material into a unitary hollow structure which is closed at the distal end thereof and which has an opening at the proximal end thereof adapted so that the cover can be fitted over a length of the blade until the distal end of the blade reaches the closed distal end of the cover, the impovement comprising:
   a. said blade having an upstanding fin which extends along the blade from the proximal end to the central portion thereof where the blade is intended to be opposite to the patient's upper front teeth during the laryngoscopic examination; and
   b. the sleeve of the blade cover having a thickened, reinforced plastic web which extends outwardly from the sleeve which fits over the fin of the blade having a thickened, reinforced flange integral with the web which extends laterally therefrom and which flexes or bends when urged against the patient's teeth to thereby avoid damage thereto.

2. The subject matter of claim 1, in which said blade includes a light exit area and in which said sleeve includes at least a portion which is transparent overlying said light exit area so that light is available when using the laryngoscope with the sleeve in place.

3. The subject matter of claim 1, in which said blade is a modification of the MacIntosh type.

4. The subject matter of claim 1, in which said blade is a modification of the Guedel type.

5. The subject matter of claim 1, in which said blade is a modification of the Miller type.

6. The subject matter of claim 1, in which said blade is a modification of various types of curved and straight blades.

* * * * *